(12) United States Patent
Stapleton et al.

(10) Patent No.: US 11,369,772 B2
(45) Date of Patent: Jun. 28, 2022

(54) CATHETER WITH MOVABLE INDICATOR

(71) Applicant: C.R. Bard Inc., Tempe, AZ (US)

(72) Inventors: Corey E. Stapleton, Gilbert, AZ (US); Claire Millar, Phoenix, AZ (US)

(73) Assignee: C.R. Bard, Inc., Tempe, AZ (US)

( * ) Notice: Subject to any disclaimer, the term of this patent is extended or adjusted under 35 U.S.C. 154(b) by 79 days.

(21) Appl. No.: 16/647,578

(22) PCT Filed: Sep. 28, 2017

(86) PCT No.: PCT/US2017/053952
§ 371 (c)(1),
(2) Date: Mar. 16, 2020

(87) PCT Pub. No.: WO2019/066847
PCT Pub. Date: Apr. 4, 2019

(65) Prior Publication Data
US 2020/0230350 A1    Jul. 23, 2020

(51) Int. Cl.
*A61M 25/00* (2006.01)
*A61M 25/01* (2006.01)
*A61M 25/02* (2006.01)
*A61M 25/09* (2006.01)

(52) U.S. Cl.
CPC ...... *A61M 25/002* (2013.01); *A61M 25/0105* (2013.01); *A61M 25/02* (2013.01); *A61M 2025/0008* (2013.01); *A61M 2025/024* (2013.01); *A61M 2025/09008* (2013.01)

(58) Field of Classification Search
CPC ............ A61M 25/002; A61M 25/0105; A61M 25/02; A61M 2025/0008; A61M 2025/024; A61M 2025/09008
USPC ..................................................... 604/100.01
See application file for complete search history.

(56) References Cited

U.S. PATENT DOCUMENTS

| | | | |
|---|---|---|---|
| 4,613,329 A | 9/1986 | Bodicky | |
| 4,757,616 A * | 7/1988 | Hills | G01B 3/04 33/488 |
| 5,611,778 A | 3/1997 | Brinon | |
| 5,657,764 A * | 8/1997 | Coulter | A61B 5/1076 606/1 |
| 6,494,848 B1 | 12/2002 | Sommercorn et al. | |
| 8,403,890 B2 | 3/2013 | King et al. | |

(Continued)

FOREIGN PATENT DOCUMENTS

| | | |
|---|---|---|
| CN | 201828350 U | 5/2011 |
| EP | 0923400 B1 | 6/1999 |

(Continued)

OTHER PUBLICATIONS

English Abstract Translation of CN201828350U dated May 11, 2011.

*Primary Examiner* — Phillip A Gray
(74) *Attorney, Agent, or Firm* — Andrew D. Dorisio; Dickinson Wright PLLC

(57) ABSTRACT

An apparatus for performing a medical procedure is provided. A catheter includes a tubular body having a plurality of markings indicative of a distance to an end portion of the catheter. A movable indicator repositionable on the tubular body to indicate a position of at least one of the plurality of markings. The indicator may also be provided with a magnifier for facilitating reading any indicia on the catheter.

21 Claims, 11 Drawing Sheets

(56) References Cited

U.S. PATENT DOCUMENTS

| | | |
|---|---|---|
| 2004/0068190 A1* | 4/2004 | Cespedes ................ A61B 8/12 600/466 |
| 2005/0065474 A1 | 3/2005 | Larson et al. |
| 2008/0051731 A1 | 2/2008 | Schwelkert et al. |
| 2008/0306408 A1 | 12/2008 | Lo |
| 2013/0267848 A1 | 10/2013 | Fearnot et al. |
| 2014/0371597 A1 | 12/2014 | Roy et al. |

FOREIGN PATENT DOCUMENTS

| | | |
|---|---|---|
| JP | 2003531675 A | 10/2003 |
| JP | 201542274 A | 3/2015 |
| WO | 2014102599 A1 | 3/2014 |

\* cited by examiner

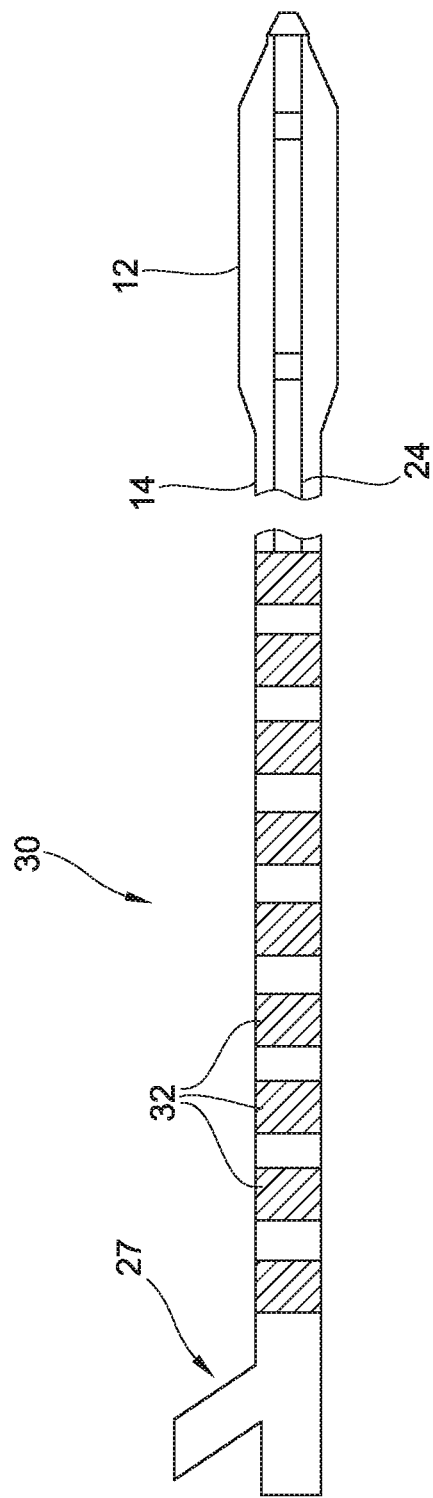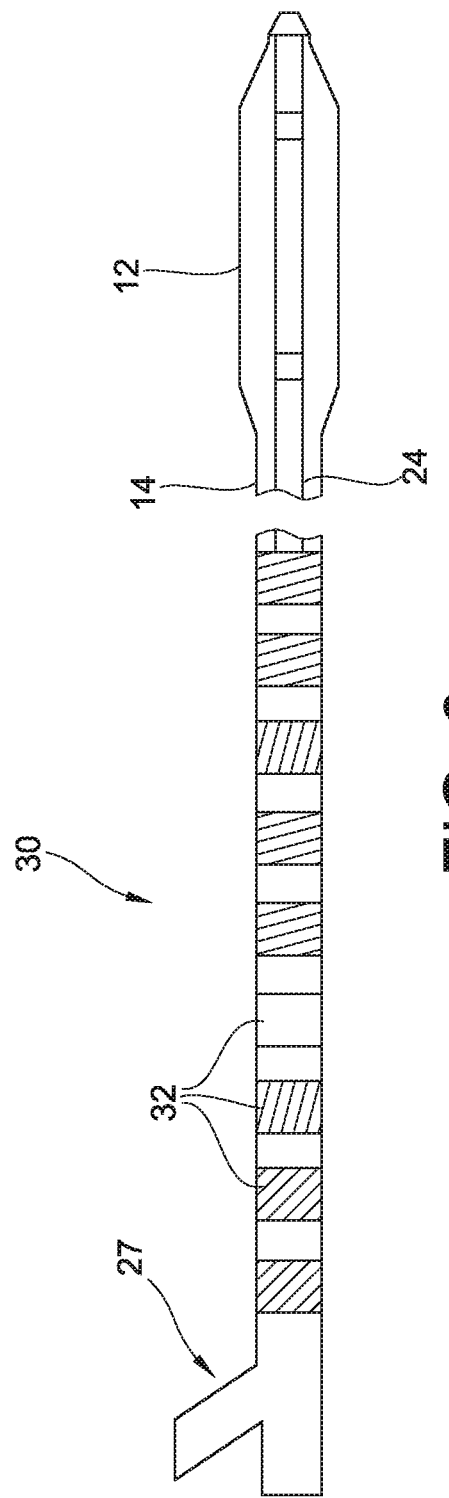

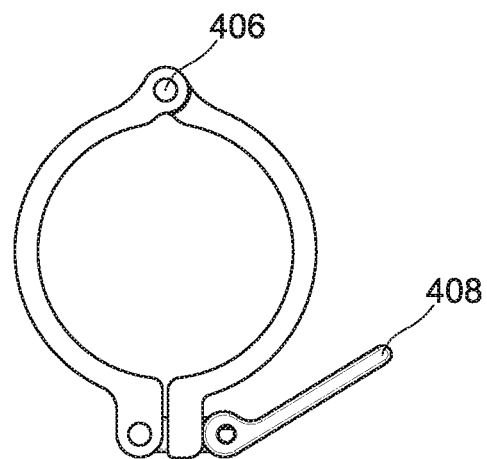
FIG. 15
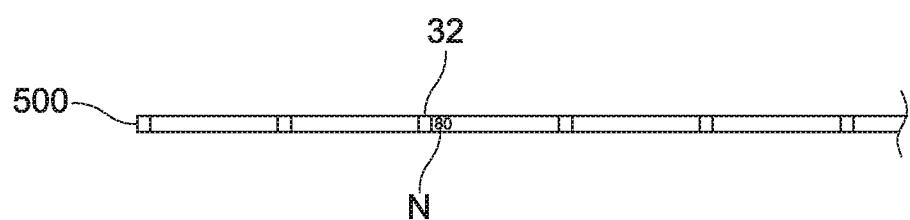
FIG. 16

CATHETER WITH MOVABLE INDICATOR

TECHNICAL FIELD

This disclosure relates generally to interventional medical procedures, such as angioplasty, and, more particularly, to a catheter adapted to assist in ensuring the proper alignment of a treatment (such as an inflatable balloon) with a treatment area.

BACKGROUND OF THE INVENTION

Catheters including balloons are routinely used to resolve or address flow restrictions or perhaps even complete blockages in tubular areas of a body, such as arteries or veins. The clinician performing the angioplasty procedure should be able to locate the position of the uninflated balloon with accuracy, so that the balloon will be properly positioned once inflated. This is conventionally accomplished by attaching radiopaque marker bands on the catheter shaft corresponding to the ends of the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

However, misalignment of the marker bands during placement along the shaft sometimes results in their failure to correspond precisely to the extent of the working surface. This misalignment may prevent the clinician from accurately identifying the location of the working surface of the balloon during an interventional procedure. Also, when successive intravascular interventions are made, such as during a pre-dilatation using a first catheter followed by dilatation using a second catheter, the clinician must guess where the pre-dilatation occurred. In either case, this uncertainty may lead to a geographic misalignment, or "miss," of the intended contact between the intended treatment area and the working surface of the balloon. It is especially desirable to avoid such an outcome when the balloon is designed to deliver a payload (such as a therapeutic agent (e.g., a drug, such as paclitaxel, rapamycin, heparin and the like), a drug, a stent, a stent graft, or a combination) or a working element (such as a cutter, focused force wire, or the like) to a specified location within the vasculature, since a miss may, at a minimum, prolong the procedure (such as, for example, by requiring redeployment of the balloon or the use of another balloon catheter in the case of a drug coated balloon), and possibly result in an inferior outcome if the lesion is not properly treated as a result of the misalignment.

Providing visible markings on a proximal portion of the catheter shaft has been proposed to facilitate inserting the catheter in a repeatable and reliable manner. Due to the use of fluoroscopy during such procedures, interventional catheters are typically employed in extremely low light conditions. Under such conditions, the markings may be difficult to perceive, especially for catheters having a particularly small size (e.g., 4 French diameter, which is approximately 0.0525 inches). Small catheters also have a reduced circumferential surface area, which of course limits the size of printing that may be used while still maintaining accuracy in terms of the measurement provided.

Accordingly, a need exists for a manner in which to position a balloon catheter into the vasculature at a treatment area with enhanced accuracy, and also in a reliable manner that is highly repeatable.

SUMMARY

One object of the invention is to provide a movable indicator for indicating a position of a marking on a catheter. Another object is to provide a movable indicator for enlarging or enhancing a clinician's viewing of indicia (such as a number) on the catheter.

According to a first aspect of the disclosure, an apparatus for performing a medical procedure is provided. The apparatus may comprise a catheter including a tubular body having a plurality of markings indicative of a distance to an end portion of the catheter, and an indicator repositionable on the tubular body to indicate a position of at least one of the plurality of markings.

In one embodiment, the indicator comprises a collar movably positioned on the tubular body (such as by sliding or being removed and repositioned). The indicator may further comprise a magnifier. The indicator may have a body including a releasable clamp for clamping the body onto the catheter. The body may include two portions connected by a hinge, or a compliant inner material.

The apparatus may further include an introducer having an entrance for receiving the catheter, and the indicator may have an outer diameter greater than a diameter of the entrance. The catheter may comprise a balloon adjacent to a distal tip, and wherein each of the plurality of markings is indicative of a distance corresponding to either a part of the balloon or the distal tip. The indicator may also only partially surround the tubular body.

A further aspect of the disclosure pertains to an apparatus for performing a medical procedure. The apparatus includes a catheter including a tubular body having at least one marking, and a magnifier connected to the tubular body for magnifying the at least one marking.

In one embodiment, the magnifier comprises a collar movably positioned on the tubular body. The collar may comprise a body including a clamp. The body may include two portions connected by a hinge, and may also include a compliant inner material.

A further aspect of the disclosure pertains to an indicator for a catheter having a marking. The indicator comprises a tubular body including a releasable clamp for securing the tubular body to the catheter. The tubular body further comprises a magnifier for magnifying the marking of the catheter.

In one embodiment, the tubular body comprises first and second portions. These portions may be connected by a hinge at one end and the releasable clamp at the other end. The tubular body may also include a compliant inner material.

Still a further aspect of the disclosure pertains to a kit, comprising: (1) a first catheter including a first repositionable indicator to indicate a first position on the first catheter; and (2) a second catheter including a second repositionable indicator to indicate a second position on the second catheter corresponding to the first position. At least one of the first movable indicator and the second movable indicator may include a magnifier. Furthermore, at least one of the first catheter and the second catheter has a tubular body supporting a balloon.

BRIEF DESCRIPTION OF THE DRAWING FIGURES

The accompanying drawing figures incorporated herein and forming a part of the specification, illustrate several aspects of the catheter with a movable indicator and, together with the description, serve to explain certain principles thereof. In the drawings:

FIGS. 5 and 6 are side views of balloon catheters with markings along a shaft;

Figure 7A:
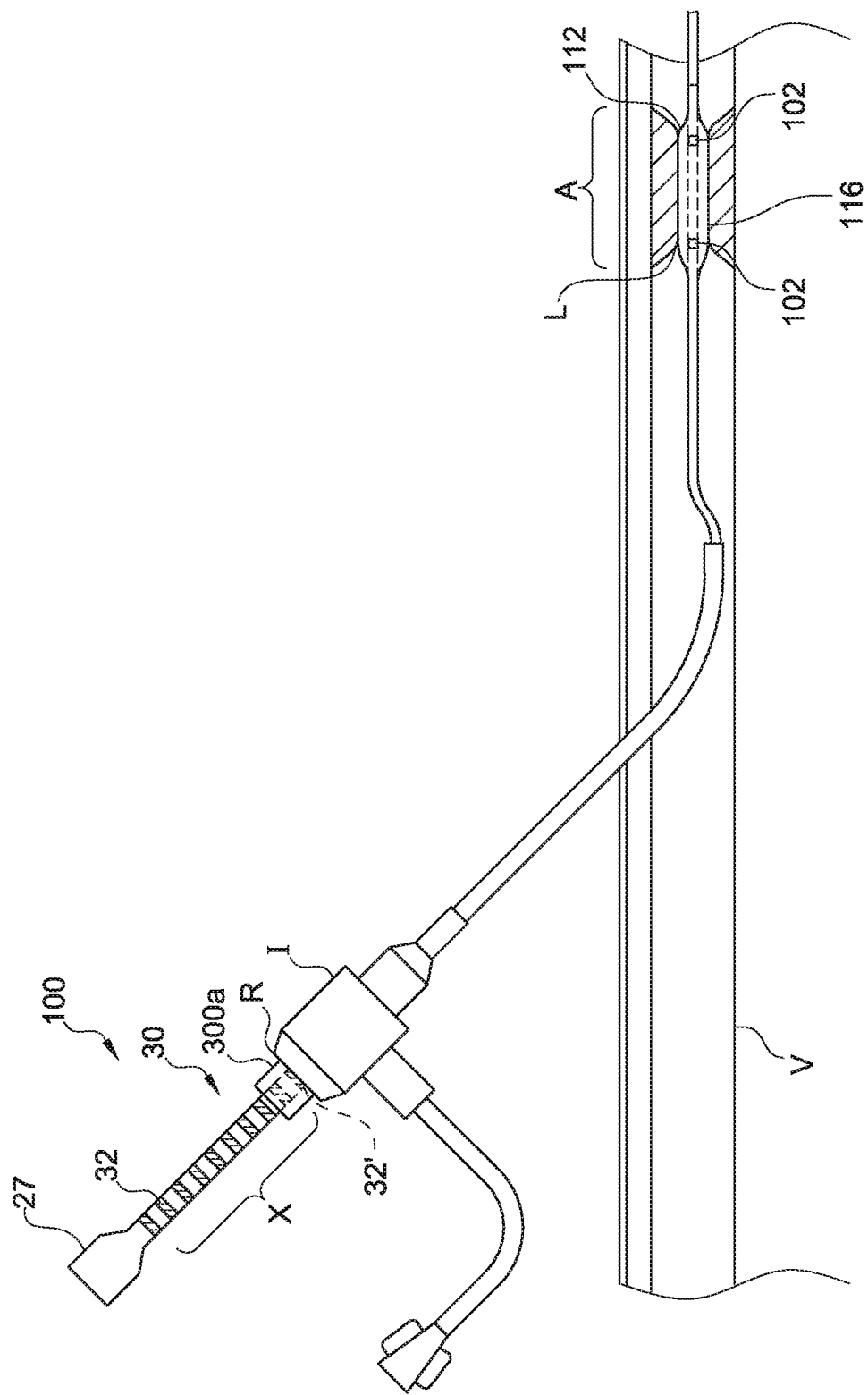
Figure 7B:
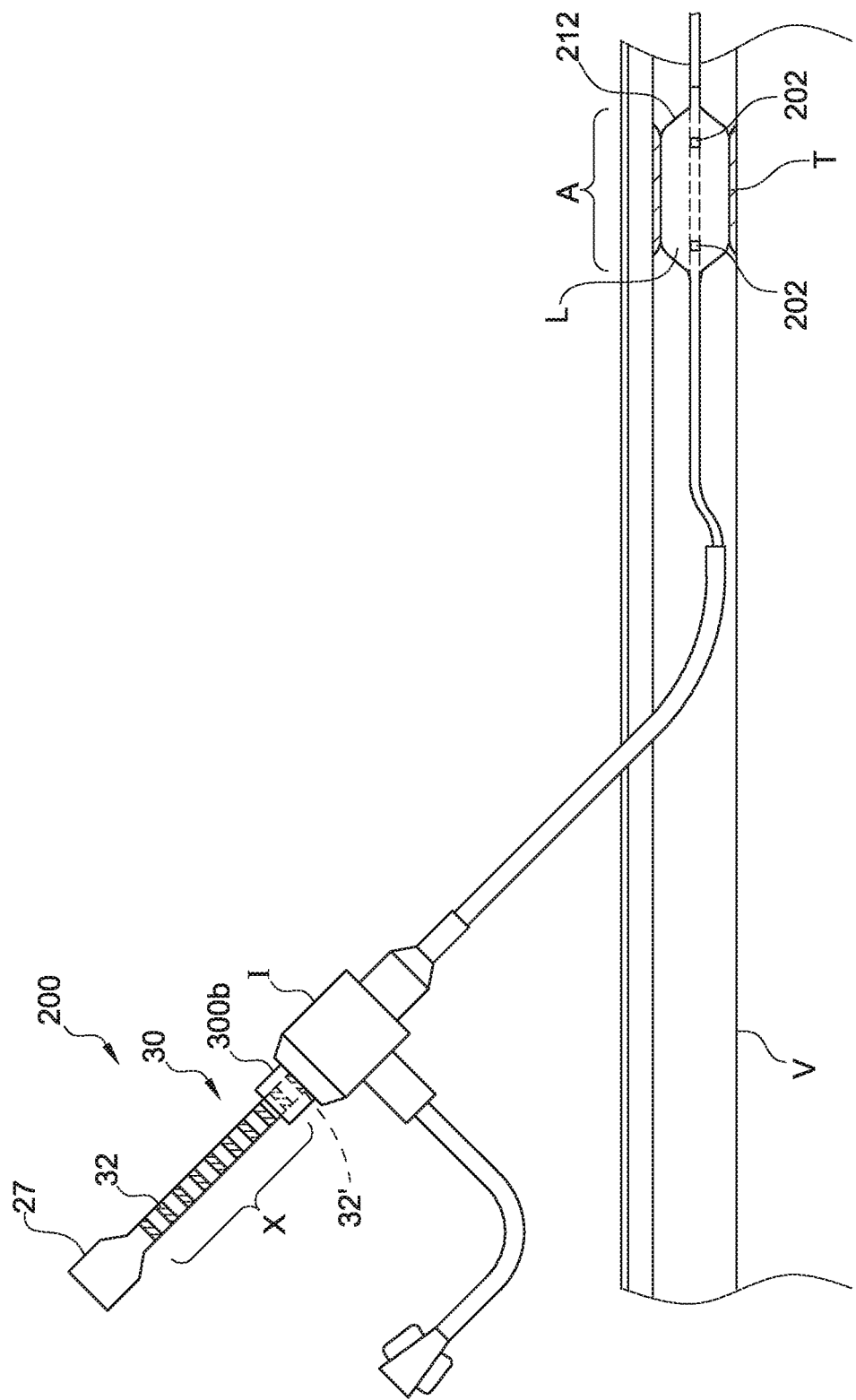
Figure 8:
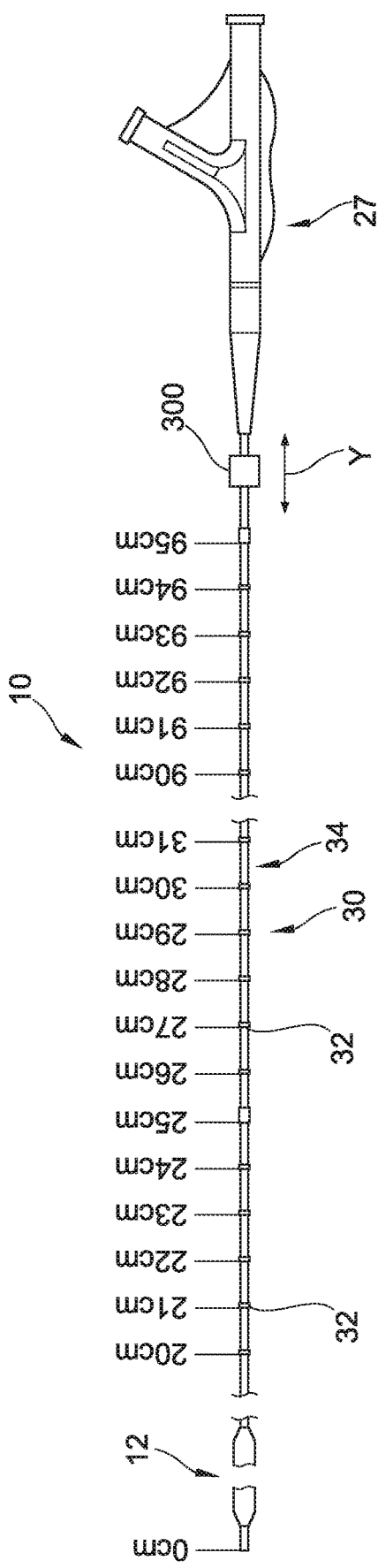
Figure 10:
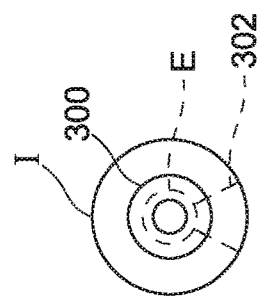
Figure 9:
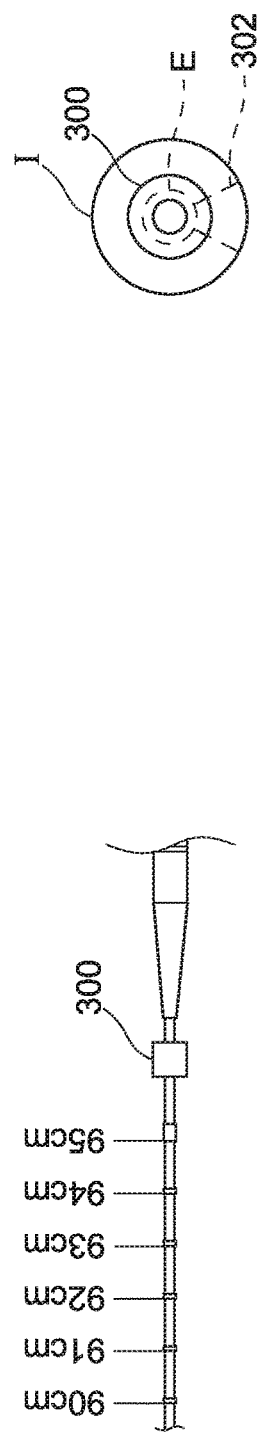
Figure 11:
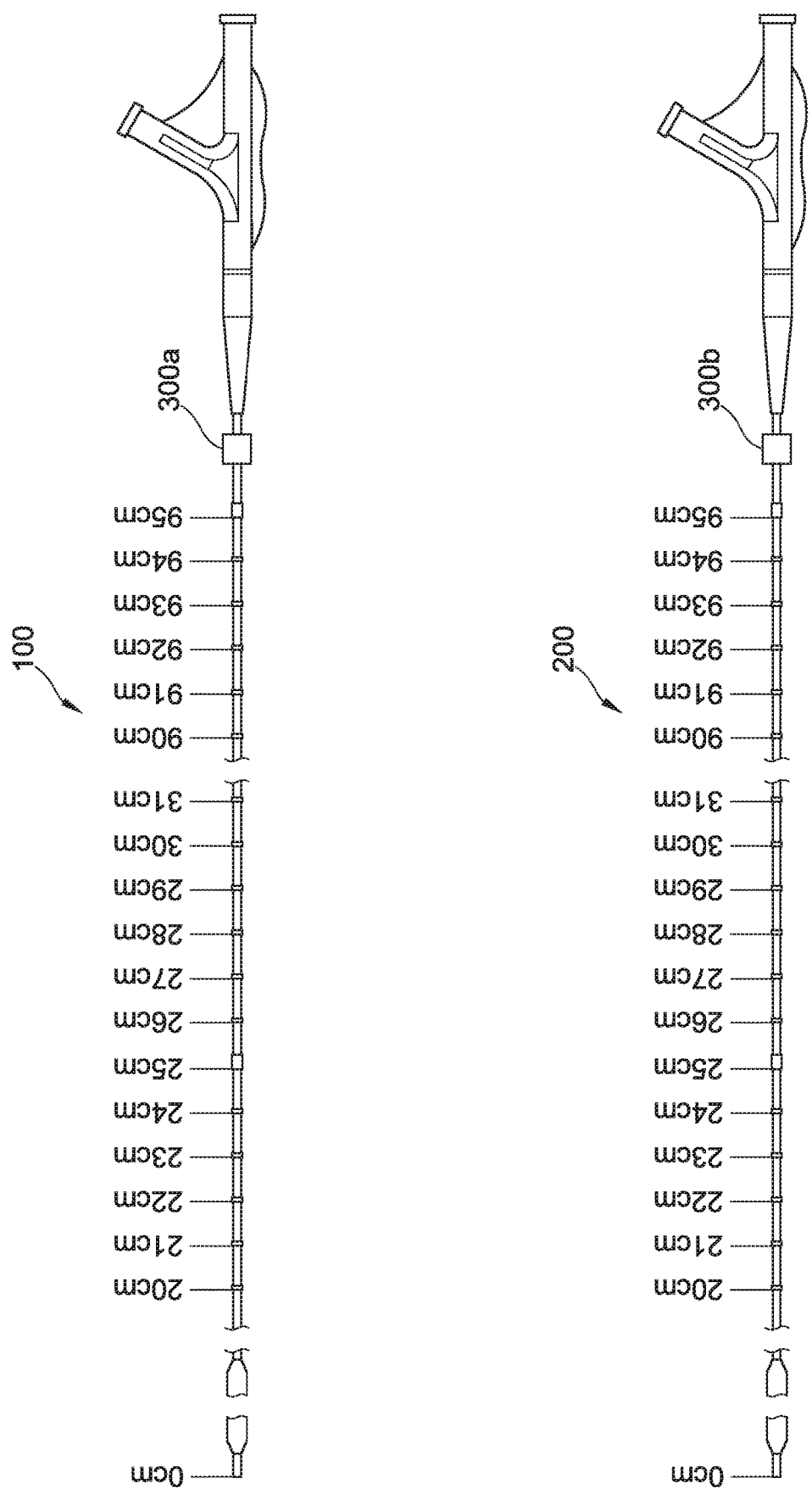
Figure 12:
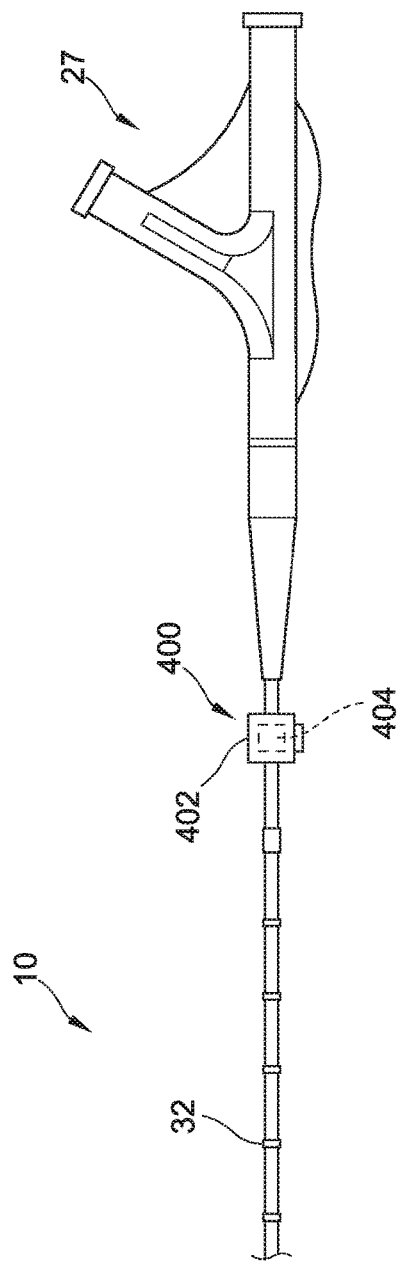
Figure 14:
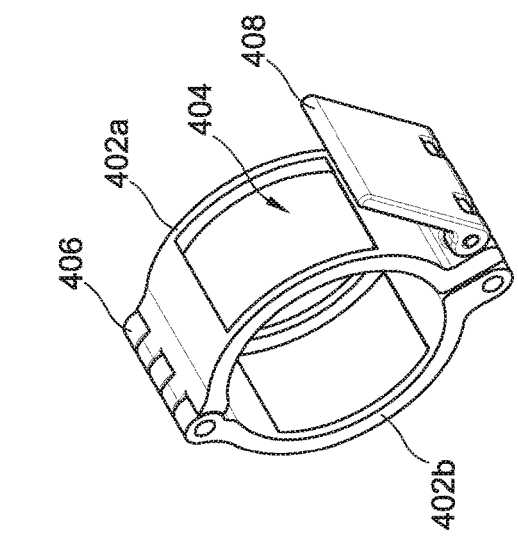
Figure 13:
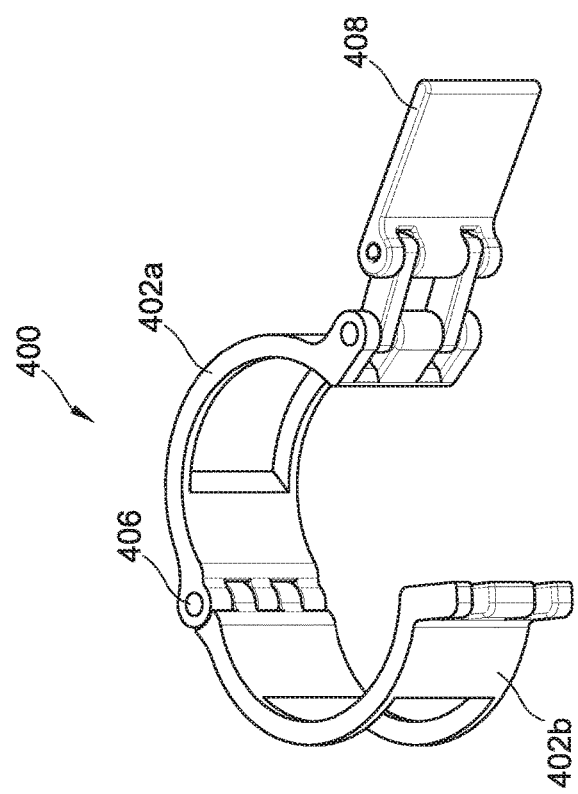
Figure 17:
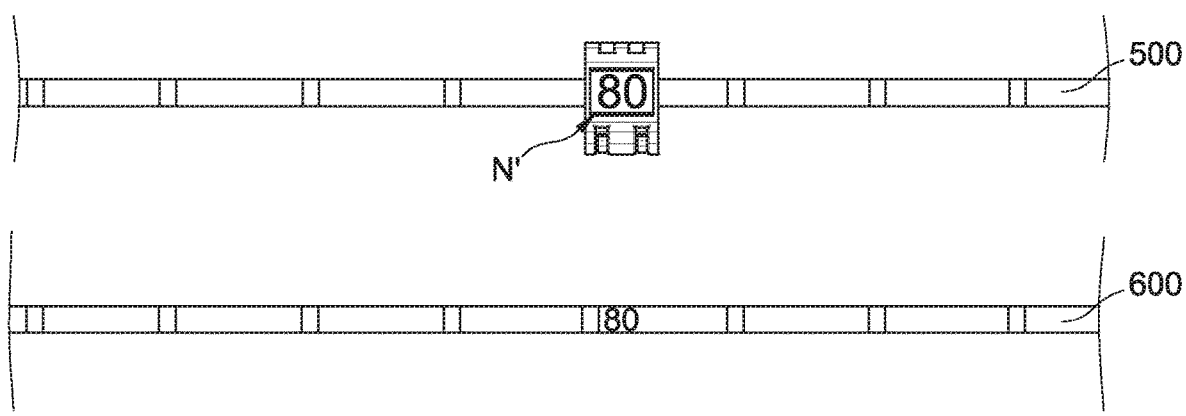

FIGS. 7A and 7B schematically illustrate possible modes of use of a balloon catheter with a movable indicator according to the disclosure;

FIGS. 8 and 9 are side and enlarged side views of a balloon catheter including a movable indicator;

FIG. 10 is a side view of the movable indicator;

FIG. 11 is a side view of two catheters including aligned movable indicators;

FIG. 12 is a partially cutaway side view of a catheter including a movable indicator having a magnifier;

FIGS. 13, 14, and 15 are perspective and side views of one embodiment of the movable indicator with a magnifier; and FIGS. 16 and 17 are photographs of two adjacent catheters having different diameters, indicating the improvement afforded by the user of the magnification proposed.

Reference will now be made in detail to the presently disclosed embodiments of the inventive aspects of the catheter with a movable indicator, examples of which are illustrated in the accompanying drawings.

DETAILED DESCRIPTION

The description provided below and in regard to the figures applies to all embodiments unless noted otherwise, and features common to each embodiment are similarly shown and numbered.

Figure 1:
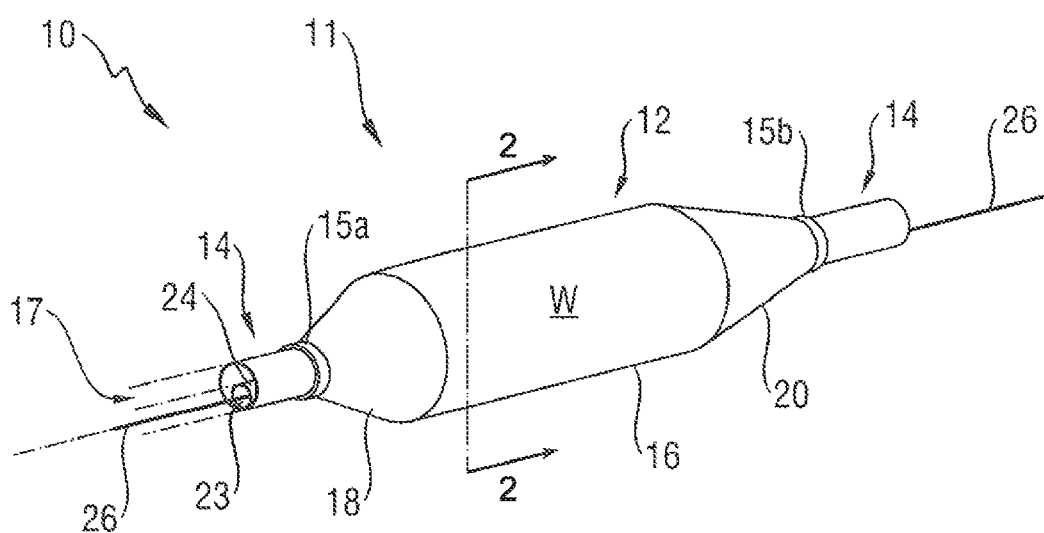
FIG. 1 is a perspective view of a partial catheter with a balloon.
Figure 2:
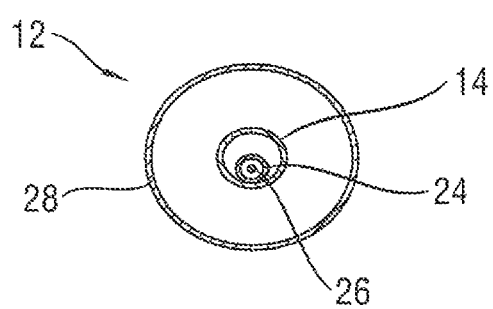
FIG. 2 is a cross-sectional view taken along line 2-2 of FIG. 1.
Figure 3:
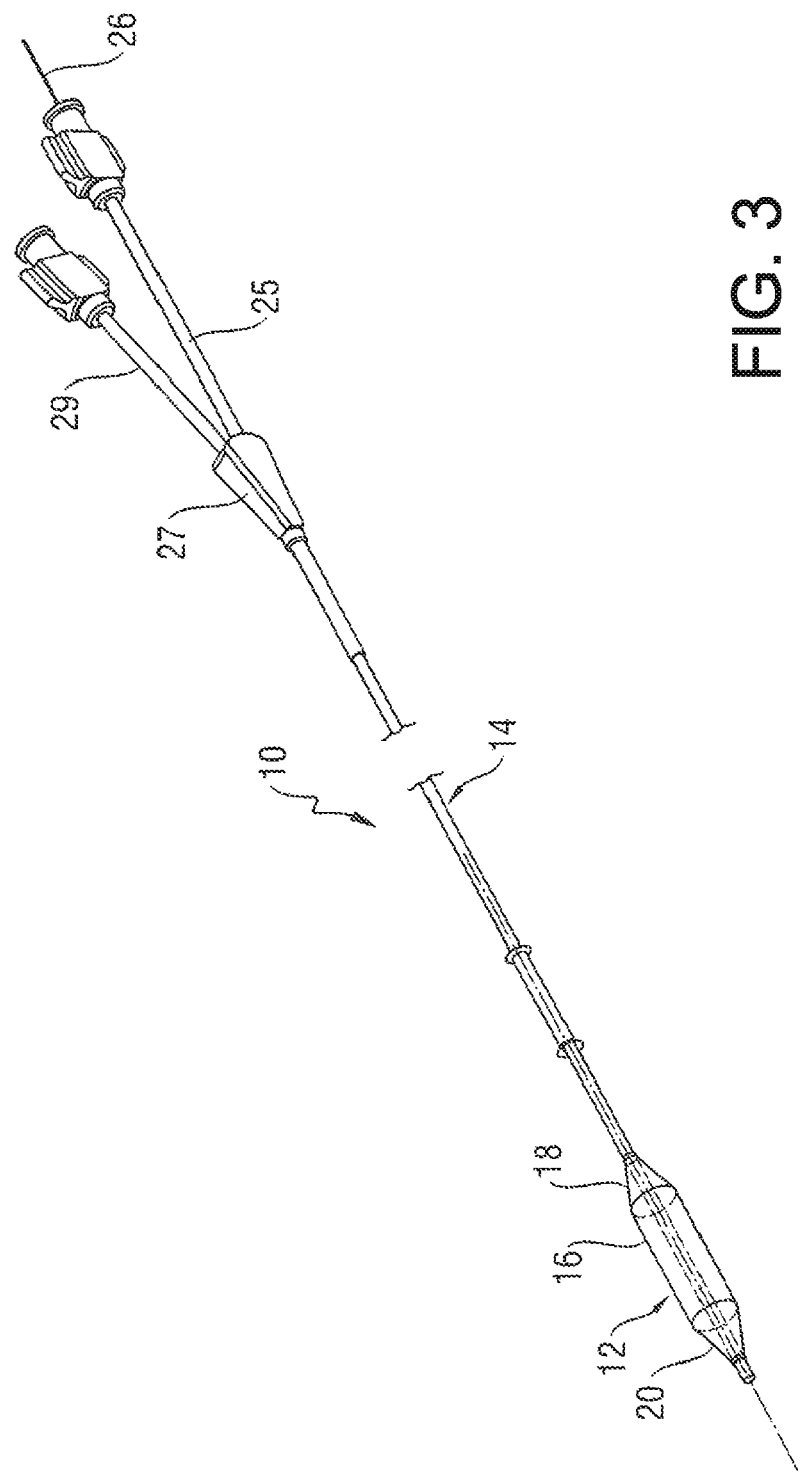
FIG. 3 is a top perspective view of a balloon catheter.

Provided is a catheter 10 having a distal portion 11 with a balloon 12 mounted on a catheter tube 14, which is a tubular body having at least one open end for receiving a fluid for use in causing the balloon to selectively inflate. Referring to FIGS. 1, 2, and 3, the balloon 12 has an intermediate section 16, or "barrel" having the working surface W, and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed to catheter tube 14 at balloon ends (proximal 15a and distal 15b) on the end sections 18, 20 to allow the inflation of the balloon 12 via one or more inflation lumens 17 extending within catheter tube 14 and communicating with the interior of the balloon 12.

Figure 4:
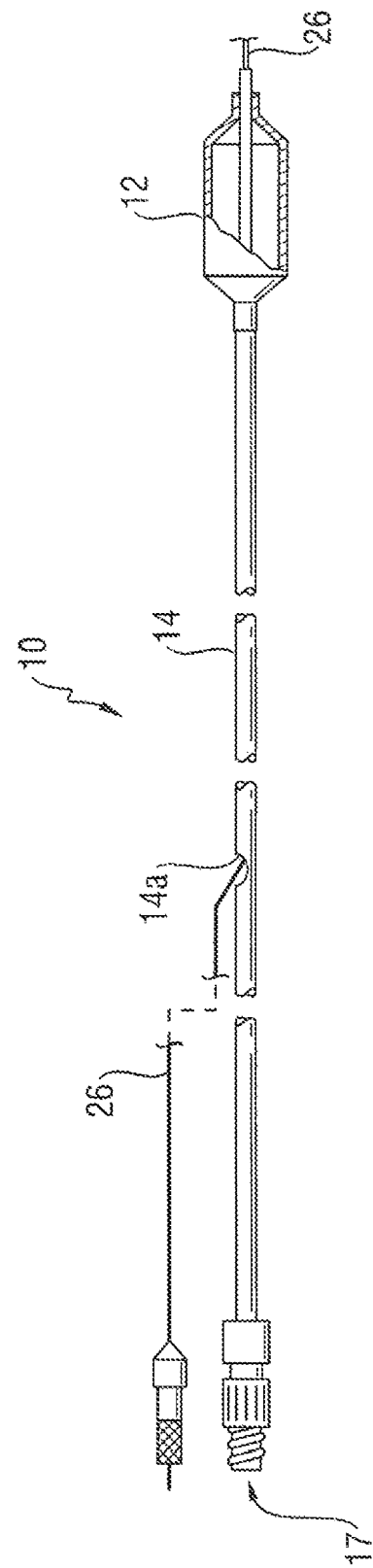
FIG. 4 is a side view of a balloon catheter.

The catheter tube 14 also includes an elongated, tubular shaft 24 forming a guidewire lumen 23 that directs the guidewire 26 through the catheter 10. As illustrated in FIG. 3, this guidewire 26 may be inserted through a first port 25 of a connector, such as a hub 27, into the lumen 23 to achieve an "over the wire" (OTW) arrangement, but could also be provided in a "rapid exchange" configuration in which the guidewire 26 enters the lumen through a lateral opening 14a closer to the distal end (see FIG. 4). A second port 29 may also be associated with catheter 10, such as by way of connector (e.g., hub 27), for introducing a fluid (e.g., saline, a contrast agent, or both) into the interior of the balloon 12 via the inflation lumen 17.

Balloon 12 may include a single or multi-layered balloon wall 28. The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined circumference that each, or together, remain constant during and after inflation. However, the balloon 12 could be semi-compliant or compliant instead, depending on the particular use. The catheter 10 may also be used in connection with a variety of treatments, including stents, stent grafts, scoring balloons, and others, without limitation.

In order to provide for enhanced locatability during an interventional procedure, the catheter 10 may be provided with a marking 30 along a portion external to the body during the procedure, such as along tube 14. As shown in FIG. 5, the marking 30 may comprise a plurality of spaced marks 32, such as bands (which may be associated with numerical distance indicators, as outlined further below). These marks 32 may extend from adjacent the connector 27 to the proximal end 15a of the balloon 12, or any portion thereof (which is considered the "proximal portion" of the catheter 10, as contrasted with the distal portion including the balloon 12). The marks 32 may be evenly or unevenly spaced (e.g., the marks may get progressively closer along the length of the shaft 24). The marks 32 may be of a single color, such as for example black as shown in FIG. 5, but as shown in FIG. 6 may also be provided in different shades or colors. The marks 32 may also comprise hash lines forming a ruler with gradations identified by numbers, letters, or symbols (see FIGS. 8-9 and 16-17). Alternatively or additionally, the marking 30 may be provided in a manner that allows for tactile engagement, such as in the forms of notches, bumps, ridges, recesses, or like structures that can be counted even when not directly visible.

In use, and with reference to FIGS. 7A and 7B, a catheter 100 including the marking 30 may be inserted in to a vessel V to a particular treatment area A, which is shown as comprising a lesion L, such as to provide a pre-dilatation assessment of its location. The catheter 100 may have a radiopaque quality (such as by providing one or more bands 102 underlying the associated balloon 112 and defining the ends of the barrel section 116, or else provided on the balloon surface or in it) that may be used in connection with fluoroscopy to determine the location of the balloon relative to the treatment area A. The skilled reader will understand from FIGS. 7A and 7B that this means that the position of the bands 102, or equivalently any sort of radiopaque marker, corresponds to the location of the treatment area A.

At this point, the clinician may view the marking 30 at a location external to the body being treated to assess the amount to which the catheter 100 has been introduced to the treatment area A. This may involve counting the marks 32 external to the introducer I (for the FIG. 5 embodiment), or else noting a particular characteristic (color or shade of a particular mark 32' for the FIG. 6 embodiment), relative to a point of reference R, such as the proximal edge of the introducer I representing a particular distance (X in the illustrated embodiment, which is the distance from the connector 27 to the reference point R).

A second catheter or treatment catheter 200 including a similar marking 30 is then used for providing a treatment T (such as a drug, a stent, a stent graft, a balloon 212 or a combination) to the treatment area A. This catheter 200 may be passed through the introducer I until the corresponding mark 32' aligns with the previously determined point of reference R, which may also correspond to distance X in the event the catheters 100, 200 are of similar lengths). The skilled reader understands from this description that by such a method of positioning, the working surface of the balloon and the treatment area A coincide substantially. The above assures the clinician that the treatment is applied to the treatment area A in the intended manner, and helps to avoid the problem of geographic misalignment. The treatment may then be provided, such as by inflating the balloon 212 of the second catheter 200 to compact the lesion L, and/or deploying the stent or stent graft. Radiopaque markers, such as bands 202, may optionally be provided to aid in confirming the location of the balloon 212 of the second catheter 200.

According to one aspect of the disclosure, a movable indicator may be provided for indicating a location on the catheter 10, such as the location of a particular mark 32 (which may correspond to a distance to the distal tip or a location on the balloon 12, such as the working surface). In one embodiment, the movable indicator comprises a stop 300 associated with the catheter 10, which may be used to control the depth of insertion. As illustrated in FIGS. 8 and 9, the stop 300 may be supported by the catheter shaft, such as tube 14, in a manner that selectively allows for relative movement to provide an indication of position of an associated structure, such as the balloon 12 or other device for providing treatment.

As shown in FIG. 10, the stop 300 may comprise an annular structure in the form of a collar with a central opening for receiving a part of the catheter 10, such as the tube 14. The stop 300 may be arranged for sliding to and fro in a longitudinal direction Y, such as from a position adjacent to the hub 27 to a proximal location closer to the proximal end 15*a* of the balloon 12. Thus, as can be appreciated, the stop 300 may have an inner diameter substantially equal to or slightly greater than the outer diameter of the tube 14, in order to create sufficient resistance to require a moderate amount of force to cause the stop 300 to move along the catheter 10 (which may be achieved or enhanced by use of materials that have a relatively high coefficient of friction, which means one sufficient to avoid free sliding movement without the input of manual force by the clinician). Moreover, the stop 300 may be of sufficient size or diameter in terms of its outer extent to engage a peripheral portion of an associated device for controlling the movement, such as the introducer I (e.g., surrounding entrance E (sometimes called a valve), as shown in FIG. 10) for receiving the proximal end portion of the tube 14 (including the balloon 12, if present)).

Referring back to FIG. 7A, in one possible mode of use, the catheter 10 may be positioned at the desired location using mark 32, with the stop 300 moved into position to assure that the proper position is maintained. But the stop could also be pre-positioned before the catheter 10 is inserted. In any case, providing or maintaining the catheter 10 at the correct location for treatment is assured as a result of the engagement with the introducer I, regardless of the ability of the clinician to perceive the marks or any associated numerical indicia corresponding to distances. The stop 300 may also facilitate reintroduction of the same catheter 10 to the same exact location during a subsequent intervention. Furthermore, in view of its sliding nature, the stop 300 may be easily repositioned by overcoming the frictional force generated with the underlying tube 14 if necessary for subsequent interventions using the same catheter 10.

As illustrated in FIG. 10 and noted above, the stop 300 may comprise a single piece of annular material, which would surround the corresponding portion of the catheter 10 (tube 14) in use. Alternatively, the stop 300 may only partially surround a portion of the catheter 10, and may thus form a semi-circular structure (as indicated by dashed lines 302 in FIG. 10). In this arrangement, the material forming the stop 300 may be resilient (polymer material, such as an elastomer (rubber)) such that it may snap or clip over the catheter 10, such as along tube 14, in a manner that permits to and fro sliding movement for purposes of being repositioned (but again, with adequate resistance to ensure that a selected position is reliably maintained during the procedure). The stop 300 serving as indicator may also take the form of a releasable clamp, such as is outlined further in the following description.

The stop 300 may be fabricated out of an inexpensive material (such as a polymer), and thus may be disposed of along with the catheter 10 once use is complete (which as noted may be a single use or multiple uses in the course of a medical procedure). As noted above, the size and material should also be designed to create sufficient friction, such that relative movement is possible when desired for manual repositioning, but resisted during a state of repose in order to indicate position. The material may also be sufficiently flexible or expandable to allow the stop 300 to pass over any enlarged structure on an end of the catheter 10, such as a folded balloon, or it may be provided on the catheter 10 before any such enlarged structure is attached during the manufacturing process.

In situations like the one described above in which two catheters 100, 200 may be used together on a single patient as part of an overall medical procedure, it can also be appreciated that an indicator, such as stop 300, may be provided on each in order to ensure the correct insertion distance is achieved during an initial and subsequent interventions. As illustrated in FIG. 11, this may involve providing a stop 300*a*, 300*b* on each catheter 100, 200, and aligning each stop at corresponding distances prior to the procedure. As can be appreciated, the stops 300*a*, 300*b* may also be arranged to correspond to each other on catheters 100, 200 without any markings, and would of course still function to ensure that the insertion distances would match. Catheters 100, 200 with stops 300*a*, 300*b* may also be provided as a single kit for use during a procedure, such as a pre-dilatation intervention and then for dilatation.

According to a further aspect of the disclosure, the catheter 10 may also be adapted for enhancing or magnifying the appearance of any indicia thereon to assist the clinician in perceiving it, especially under low light conditions and/or when particularly small diameter catheters are employed. In one embodiment, as shown in FIG. 12, this function is provided by an indicator in the form of a magnifier 400, which like stop 300 may be positioned along the catheter 10, such as over tube 14. Referring to FIGS. 13, 14, and 15, the magnifier 400 may include a tubular or annular body 402 for receiving the catheter 10, and a magnifying window or lens 404 through which a surface portion of the catheter, such as along tube 14, may be perceived in an enlarged manner as a result of the enlargement or magnification provided. Accordingly, the clinician using the catheter can be assured of the proper positioning of the catheter 10 in the vasculature using the marks 32, which as noted above may include numerical indicia corresponding to distance measurements.

As also indicated in FIGS. 13, 14, and 15, the body 402 may comprise a two piece arrangement, formed of connected portions 402*a*, 402*b*, which are shown as being partly circular but may take other shapes as well. The connection may be established by way of a hinge 406 (which is shown as being formed by interdigitating parts, but could be a flexible or living hinge as well), and a releasable clamp 408 may be provided for causing the body portions 402*a*, 402*b* to close and form a smaller diameter for gripping an external surface of the catheter 10 when actuated, or an enlarged diameter for allowing repositioning when released. In this manner, the magnifier 400 may be enlarged for positioning over the catheter 10, such as along tube 14, positioned as desired when the appropriate distance measurement is seen through lens 404 (which may comprise a clear plastic material incorporated into the body 402, but the entire body could also be formed of a material having a magnifying capability), and then left in position during use. Indeed, it can be appreciated that the magnifier 400 may also function in the same manner as stop 300, and thus provide an assurance that the proper insertion distance is achieved as a result of the engagement with a corresponding part of an associated structure, such as introducer (see FIGS. 7A and 7B). The interior surface of the body 402, such as along portions 402a, 402b, may also optionally be lined with a relatively soft or compliant material (e.g., a polyether block amide, such as a PEBAX material) to create a degree of give when the clamp 408 is secured over the tube 14, and thus allow for use in connection with a variety of catheters despite variances in diameter.

FIGS. 16 and 17 illustrate the nature of the improvement afforded by the use of a magnifier 400. A first catheter 500 depicted in FIG. 16 is a 4 French diameter, and a second catheter 600 is a 5 French diameter. It can be appreciated the number N is much smaller on the 4 French version, and more difficult to perceive, even under normal lighting. Placing the indicator with the magnifying lens 404 over the first catheter 500 substantially enlarges the marking (see magnified number N'), making it at least as large as the number on the second, larger catheter 600 and much easier to perceive, especially in lower light conditions.

In summary, a catheter 10 adapted for being inserted into the vasculature a particular distance, as determined by an associated movable indicator. In one embodiment, the indicator comprises a repositionable stop 300 that may be used to mark a particular distance along the catheter 10, such as associated with a particular marking 30. In another, the indicator is a repositionable magnifier 400 that may be used to enlarge the appearance of any indicia on a catheter, such as along the shaft or tube 14 for denoting insertion distance, and which may also function as a stop for determining or indicating an insertion distance for an associated catheter.

While the disclosure presents certain embodiments to illustrate the inventive concepts, numerous modifications, alterations, and changes to the described embodiments are possible without departing from the sphere and scope of the present invention, as defined in the appended claims. For example, the magnification feature may be applied to the stops 300a, 300b used in the kit of FIG. 11. The indicator (stop 300 or magnifier 400) may also be formed of a photo or chemiluminescent material or lighted to facilitate visibility in low light conditions. Any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

What is claimed:

1. An apparatus for performing a medical procedure, comprising:
    a catheter including a tubular body having a plurality of markings indicative of a distance to an end portion of the catheter; and
    an indicator comprising two partly circular body portions connected by way of a hinge, the indicator further comprising a releasable clamp for causing the body portions to close and form a smaller diameter when actuated, said indicator being repositionable on the tubular body to indicate a location of at least one of the plurality of markings, wherein the indicator comprises a magnifier; and
    an introducer having an entrance for receiving the catheter, the indicator having an outer diameter greater than a diameter of the entrance.

2. The apparatus of claim 1, wherein the indicator comprises a collar movably positioned on the tubular body.

3. The apparatus of claim 1, wherein the indicator comprises a body including a releasable clamp for clamping the body onto the catheter.

4. The apparatus of claim 3, wherein the body includes two portions connected by a hinge.

5. The apparatus of claim 1, wherein the indicator includes a compliant inner material.

6. The apparatus of claim 1, wherein the indicator only partially surrounds the tubular body of the catheter.

7. The apparatus of claim 1, further including an introducer having an entrance for receiving the catheter, the indicator having an outer diameter greater than a diameter of the entrance.

8. The apparatus of claim 1, wherein the catheter includes a balloon adjacent to a distal tip, and wherein each of the plurality of markings is indicative of a distance corresponding to either a part of the balloon or the distal tip.

9. The apparatus of claim 1, wherein the indicator is adapted for sliding along the body.

10. An apparatus for performing a medical procedure, comprising:
    a catheter including a tubular body having at least one indicia;
    an indicator slidably engaging the tubular body and selectively fixable to the tubular body, the indicator comprising two partly circular body portions connected by a hinge and further comprising a releasable clamp for causing the body portions to close and form a smaller diameter when actuated; and
    a magnifier connected to the tubular body for magnifying the at least one indicia.

11. The apparatus of claim 10, wherein the indicator includes a compliant inner material.

12. The apparatus of claim 10, wherein the indicia comprises a number.

13. An indicator for a catheter having a marking, comprising:
    a tubular body formed by two partly circular body portions connected by a hinge, the tubular body further including a releasable clamp for causing the body portions to close and form a smaller diameter when actuated, said releasable clamp for securing the tubular body to the catheter, wherein the tubular body further comprises a magnifier for magnifying the marking of the catheter.

14. The indicator of claim 13, wherein the tubular body includes a compliant inner material.

15. A kit, comprising:
- a first catheter including a first repositionable indicator to indicate a first position on the first catheter, said first repositionable indicator formed of two partly circular body portions connected by a hinge, the indicator further including a releasable clamp for causing the body portions to close and form a smaller diameter when actuated; and
- a second catheter including a second repositionable indicator to indicate a second position on the second catheter corresponding to the first position.

16. The kit of claim 15, wherein at least one of the first movable indicator and the second movable indicator includes a magnifier.

17. The kit of claim 15, wherein at least one of the first catheter and the second catheter has a tubular body supporting a balloon.

18. The kit of claim 15, wherein the first and second catheter include a proximal end portion having plurality of matched markings indicating a distance to a distal end portion of the catheter.

19. The apparatus of claim 1, wherein the indicator comprises two partly circular body portions connected by a hinge, and further comprises a releasable clamp for causing the body portions to close and form a smaller diameter when actuated.

20. The apparatus of claim 19, wherein at least one of the body portions comprises the magnifier, said magnifier comprising a lens.

21. The apparatus of claim 19, wherein both of the two partly circular body portions form a body, and wherein the body is formed of a material having magnifying capability.

\* \* \* \* \*